United States Patent [19]

Peterson

[11] Patent Number: 5,277,581
[45] Date of Patent: Jan. 11, 1994

[54] ORTHODONTIC HEADGEAR ASSEMBLY WITH MAGNETIC RELEASE MECHANISM

[75] Inventor: Jeff Peterson, Aurora, Colo.

[73] Assignee: RMO, Inc., Denver, Colo.

[21] Appl. No.: 2,425

[22] Filed: Jan. 8, 1993

[51] Int. Cl.5 .............................................. A61C 7/00
[52] U.S. Cl. ................................................... 433/5
[58] Field of Search ............................. 433/5, 17, 189

[56] References Cited

U.S. PATENT DOCUMENTS

| | | | |
|---|---|---|---|
| 3,186,089 | 6/1965 | Asher | 32/14 |
| 4,087,915 | 5/1978 | Andrews | 32/14 |
| 4,115,921 | 9/1978 | Armstrong | 32/14 |
| 4,155,161 | 5/1979 | Armstrong | 32/14 |
| 4,212,637 | 7/1980 | Dougherty et al. | 433/5 |
| 4,215,983 | 8/1980 | Frazier | 433/5 |
| 4,226,589 | 10/1980 | Klein | 433/5 |
| 4,238,188 | 12/1980 | Armstrong | 433/5 |
| 4,368,039 | 1/1983 | Armstrong | 433/5 |
| 4,402,669 | 9/1983 | Frazier | 433/5 |
| 4,416,625 | 11/1983 | Armstrong | 433/5 |
| 4,764,110 | 8/1988 | Dougherty | 433/5 |
| 4,872,836 | 10/1989 | Grove | 433/5 |

Primary Examiner—Gene Mancene
Assistant Examiner—Nicholas D. Lucchesi
Attorney, Agent, or Firm—Sheridan Ross & McIntosh

[57] ABSTRACT

An orthodontic headgear assembly which incorporates at least one magnetic release mechanism. In one embodiment, the headgear assembly generally includes an inner bow, an outer bow interconnected with the inner bow, a mechanism for generating and applying a force to the ends of the outer bow which is thus transferred to the patient's teeth, and a magnetic release mechanism which is positioned between each end of the outer bow and the force generating mechanism. When a given magnetic release mechanism is subjected to a force of a predetermined magnitude, the mechanism disconnects adjacent portions of the headgear assembly to reduce the potential for the adverse effects on the patient due to snapback of the outer and/or inner bow when at least a portion of the force is removed from the headgear assembly.

30 Claims, 9 Drawing Sheets

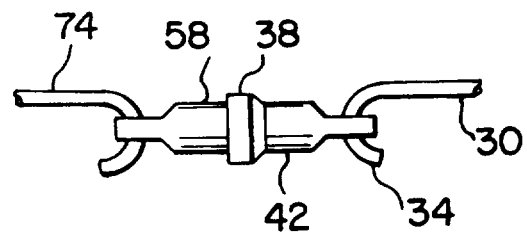
FIG. IA
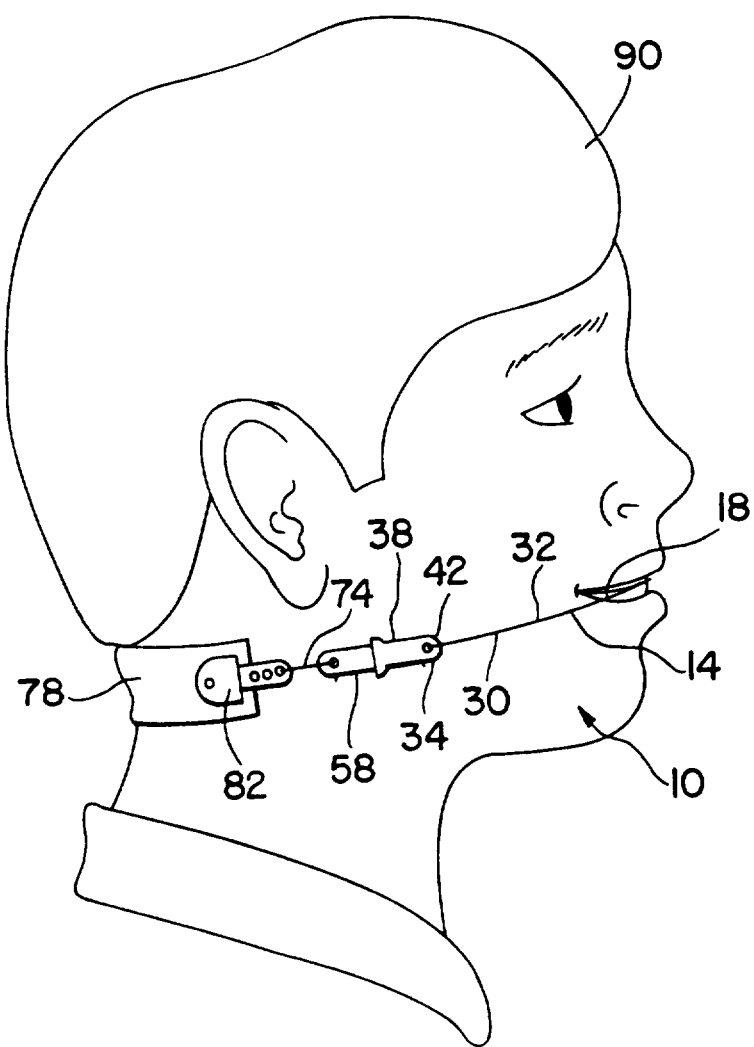
FIG. I

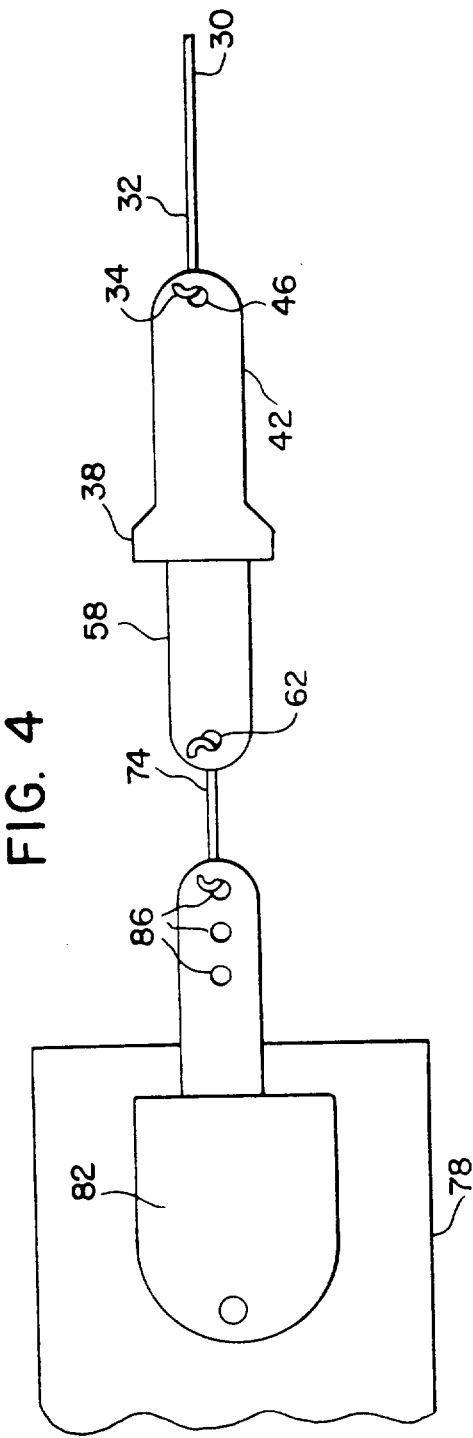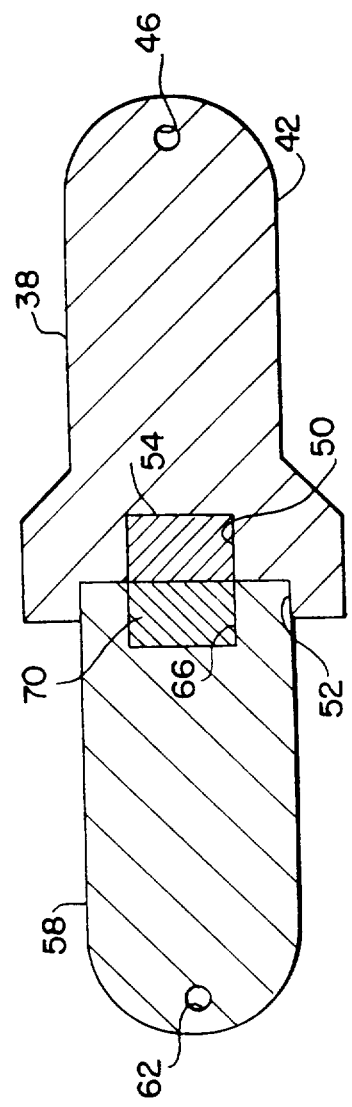
FIG. 4
FIG. 3

ORTHODONTIC HEADGEAR ASSEMBLY WITH MAGNETIC RELEASE MECHANISM

FIELD OF THE INVENTION

The present invention generally relates to the field of orthodontic headgear assemblies and, more particularly, to such assemblies which incorporate at least one magnetic release mechanism to disconnect the assembly when a force of a predetermined magnitude is applied thereto, but which still accommodates for the application of a variety of orthodontic treatment forces to the patient.

BACKGROUND OF THE INVENTION

Headgear assemblies are commonly used in orthodontic treatment to apply forces to a patient's teeth to accomplish specific types of tooth movements. Such headgear assemblies typically include an inner bow, an outer bow, and some type of a neck/head strap assembly. More particularly, the two ends of the inner bow are each typically inserted into a buccal tube attached to one of the upper first molars. Moreover, the outer bow is connected to the inner bow and extends at least partially about both sides of the patient's face such that the ends of the outer bow may be engaged by the neck/head strap assembly. The neck/head strap assembly is generally formed at least in part from an elastic material or other energy-storing mechanism so as to be capable of stretching and thus applying the desired treatment forces to each of the ends of the outer bow. These treatment forces are then typically transmitted to the upper first molars and any teeth interconnected therewith (e.g., via an archwire and/or other appropriate connectors).

The manner in which the above-described treatment forces are applied to the patient's teeth utilizing a headgear assembly may be varied to achieve the particular desired orthodontic treatment objectives. For instance, the force vectors which are utilized will affect the type of tooth movement achieved. A substantially purely distal or rearward force may be applied to the patient's teeth (i.e., a distal force vector) by positioning a neck strap about the back of the patient's neck and substantially within the occlusal plane for engaging the outer bow to achieve substantially only a distal tooth movement. In the event that a substantially symmetrical outer bow is utilized, substantially equal forces will be applied to each of the upper first molars. Although this substantially symmetrical distal pull may satisfy the treatment objectives in a number of patient cases, quite often various combinations of tooth intrusion/extrusion, as well unilateral or bilateral bodily movements of single or groups of teeth are required for an individual patient's treatment objectives.

In order to provide for the above-described multiple force delivery capabilities, headgear assemblies may incorporate a head strap assembly (e.g., a head cap), such as is generally illustrated in U.S. Pat. No. 3,186,089 to Asher, issued Jun. 1, 1965. With this type of a device, both distally and vertically directed force components can be effectively applied to the patient's teeth. By varying the location or angle at which the vertical force component is coupled relative to the occlusal plane, the above-described different types of tooth movements may be achieved. For instance, by applying the vertical force component mesially (i.e., forward) of the upper first molars which are again directly engaged by the inner bow, the upper first molars may be tipped distally (a distal root tip) while being bodily moved distally. Similarly, if the vertical force component is applied distally (i.e., rearward) of the upper first molars, the upper first molars may be tipped mesially (a mesial root tip) while being bodily moved distally.

In addition to varying the vectors of the treatment force to achieve a particular combination of simultaneous tooth movements, variations in force magnitudes applied to the upper first molars may also be utilized to achieve a desired result in orthodontic treatment planning. For instance, in some instances the forces which are applied to the upper first molars and teeth interconnected therewith are substantially equal, typically by utilizing a substantially symmetrical outer bow. However, there are also instances where it is desirable to apply a greater force on one side of the patient's mouth than on the other side such that one of the upper first molars and its interconnected teeth experience greater forces than the other upper first molar/interconnected teeth to achieve greater tooth movement. This technique is typically accomplished by utilizing an outer bow having different length arms (e.g., the arm being defined as the distance from where the outer bow is connected to the inner bow to the end of the outer bow), and/or by having one of the arms of the outer bow "bowed" to a greater degree than the other arm, and/or by various combinations thereof.

One of the problems generally associated with headgear assemblies in achieving a given treatment effect is that they are potentially hazardous to the patient from a health standpoint. More particularly, upon the application of external, non-orthodontic treatment forces to the headgear assembly, typically by a third party grabbing the patient's outer bow and exerting a force thereon, the potential exists for the inner and/or outer bow to undesirably impact the patient upon release of the external force if the treatment forces continue to be applied to the outer bow. This of course creates a risk for significant injury to the patient. For instance, if the outer bow is pulled out far enough so that the ends of the inner bow disengage the buccal tubes, the subsequent "snapback" of both the inner and outer bows upon termination of the application of the external force (e.g., by a disengagement of the outer bow by the third party), which is caused by the continued engagement of the outer bow by the neck/head strap assembly, is likely to cause damage to the soft tissue of the mouth by the impacting of the inner bow thereon. If the outer bow is pulled so that the ends of the inner bow actually extend outside the mouth prior to the termination of the application of the external force, injury to the patient's face or eyes may result due to the subsequent and above-described snapback and any resulting impingement of the inner and/or outer bow with the patient. As can be appreciated, neither of these scenarios is desirable in maintaining the safety of the patient at an acceptable level during orthodontic treatment. Therefore, headgear assemblies have incorporated some type of release mechanism to disconnect the assembly prior to the time at which an increased health risk to the patient exists due to these types of circumstances.

There are a variety of headgear assemblies available which utilize various type of mechanical releases. Generally, these mechanical releases are relatively complex from both a structural and thus manufacturing standpoint. Consequently, manufacturing costs may be undesirably increased. Moreover, these releases are subject to material fatigue (e.g., wear) due to the relatively high treatment forces involved and based upon the manner in which such releases function (e.g., utilizing a compression of members to pass through a opening to provide the disconnection), as well as contamination (e.g., collection of dirt/debris within the release). In addition, some of these releases are subject to patient manipulation. In any case, the point at which release occurs may be undesirably affected (e.g., it may increase or decrease via fatigue, contamination, and/or patient manipulation). U.S. Pat. No. 4,115,921 to Armstrong, issued Sep. 26, 1978; U.S. Pat. No. 4,238,188 to Armstrong, issued Dec. 9, 1980; U.S. Pat. No. 4,368,039 to Armstrong, issued Jan. 11, 1983; U.S. Pat. No. 4,155,161 to Armstrong, issued May 22, 1979; U.S. Pat. No. 4,215,983 to Frazier, issued Aug. 5, 1980; U.S. Pat. No. 4,402,669 to Frazier, issued Sep. 6, 1983; U.S. Pat. No. 4,226,589 to Klien, issued Oct. 7, 1980; U.S. Pat. No. 4,416,625 to Armstrong, issued Nov. 22, 1983; and U.S. Pat. No. 4,872,836 to Grove, issued Oct. 10, 1989, are generally representative of these types of mechanical release mechanisms.

Another type of a "release" mechanism for a headgear assembly is disclosed by U.S. Pat. No. 4,764,110 to Dougherty, issued Aug. 16, 1988. Dougherty discloses a headgear assembly in which the inner bow is detachably connected to displaced molars within a patient's mouth by a combination of buccal tubes and attractively engaged magnets. More particularly, a magnet is positioned on each side of the inner bow and on the buccal tubes as well such that when each buccal tube receives an end of the inner bow, the magnets come into contact. A magnet is also positioned on each of the inner and outer bows to attractively intercouple the same. These particular magnets may be positioned within a box-shaped retainer so as to confine the relative motion of such magnets, as well as the inner and outer bows, to lineal motion. An elastic band traverses the back of the patient's head and engages the ends of the outer bow to provide the treatment force thereto. By utilizing this configuration, the disclosure of Dougherty indicates that the separation of the inner and outer bows can be positively assured upon application of a predetermined force.

Based upon the foregoing and the illustrated configuration of Dougherty, it can be appreciated that none of the magnetic interconnections suggested by Dougherty affect the application of treatment forces to the outer bow by the elastic band. More particularly, regardless of whether the inner bow/buccal tube magnetic connection or the inner bow/outer bow magnetic connection releases at the described time, forces continue to be applied to the outer bow by the elastic band such that the potential for injury to the patient still exists due to the above-described snapback. Moreover, the types of treatment forces applied to the outer bow may have an effect on the point at which the described release occurs in the Dougherty configuration. For instance, the utilization of a treatment force having both distal and substantial vertical components may alter the release point by introducing binding (if the box-shaped retainer is incorporated which again limits relative motion to a line as noted) and/or by subjecting the magnetic interconnection between the inner and outer bows to compressive, torsion, and/or shear-type forces/stresses. Similar effects may be evident if "different" forces are applied to the ends of the outer bow as described above (e.g., by having the outer bow arms be of different lengths, being bowed to differing degrees, and/or a combination thereof).

SUMMARY OF THE INVENTION

The present invention is an orthodontic headgear assembly that "releases" upon the application of a force of a predetermined magnitude to the assembly (or at least a portion thereof). More particularly, the present invention accommodates for the particular level of treatment forces being used, but will release the assembly/terminate the application of treatment forces when the total forces experienced by at least a portion of the assembly exceeds the treatment forces by a predetermined amount. For instance, the total forces experienced by the assembly include the treatment forces and any force applied by a third party grabbing and pulling the assembly or portions thereof.

Generally, the assembly includes an inner bow which transfers and applies a treatment force to the patient's teeth, an outer bow connected to the inner bow, a device for generating and applying a treatment force to the ends of the outer bow which is thus transferred to the inner bow, and at least one magnetic release mechanism which disconnects adjacent portions of the assembly under the described condition. Therefore, the present invention incorporates a desirable safety feature for a commonly used type of orthodontic treatment.

In one aspect of the present invention, the magnetic release mechanism is positioned so as to discontinue the application of the treatment force to the outer bow under the above-described condition. In another aspect, the magnetic release mechanism is positioned so as to be subjected to substantially only tensile forces during treatment, and preferably regardless of the vector of the treatment force and/or any variation in the magnitude of treatment forces applied to the displaced teeth of the patient directly engaged by the inner bow (e.g., the upper first molars); considering, however, that the strength of the magnetic release mechanism is selected/calibrated for its associated treatment force. In still another aspect, the predetermined magnitude at which the magnetic release mechanism releases the assembly will remain substantially constant and not substantially affected by the vector of the treatment force and/or by any variation in the magnitude of the treatment forces applied to the described displaced teeth once the strength of the magnetic release mechanisms are appropriately selected.

One embodiment which accommodates for each of these aspects generally is provided by rigidly interconnecting the outer and inner bows and utilizing a magnetic release mechanism between each end of the outer bow and an elastic neck/head strap assembly or a neck/head strap assembly which incorporates some other type of energy storing material. Various configurations of outer bows (e.g., different length arms, arms bowed in differing degrees, and/or combinations thereof) and various treatment force vectors may thus be utilized without substantially affecting the disconnection function provided by the magnetic release mechanisms since each release mechanism is axially aligned purely within the tensile treatment force vector. In this regard, it may be desirable/required to have one of the magnetic release mechanisms be stronger than the other to accommodate for different forces being applied to the ends of the outer bow (i.e., one of the release mechanisms may have a higher release force than the other).

BRIEF DESCRIPTION OF THE DRAWINGS

FIG. 1 is a side view of a patient wearing one embodiment of the headgear assembly of the present invention which may provide for a substantially straight distal pull to the patient's teeth;

FIG. 1A is an enlarged side view of the interconnection of the magnetic release mechanism within the assembly of FIG. 1;

FIG. 3 is a longitudinal, cross-sectional view of one embodiment of a magnetic release mechanism;

FIG. 4 is an enlarged view of one embodiment of an interconnection between an outer bow and a neck/head strap provided by a magnetic release mechanism;

DETAILED DESCRIPTION

The present invention will be described with reference to the accompanying drawings which assist in illustrating the pertinent features thereof. Generally, the present invention is an orthodontic headgear assembly which incorporates at least one magnetic release mechanism to disconnect the assembly upon the application of a non-orthodontic treatment force of a predetermined magnitude to the assembly or at least a portion thereof, such as by disconnecting the orthodontic treatment forces. More particularly, the magnetic release mechanism has a release force which is greater than the treatment forces to be used by a predetermined magnitude. Therefore, in the event that a third party grabs and pulls upon the assembly to increase the forces experienced by the assembly by at least this predetermined magnitude, the assembly will disconnect to reduce the potential of the patient being injured by the third-party activity.

Figure 2:
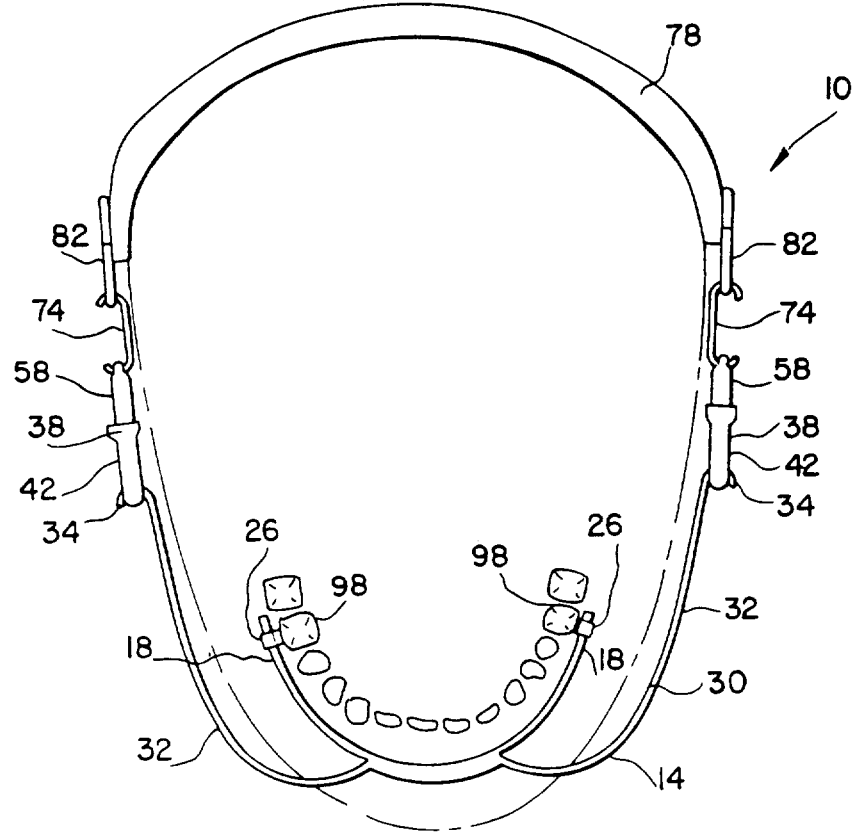
FIG. 2 is a view of the headgear assembly of FIG. 1 installed on a patient's upper arch.
Figure 2A:
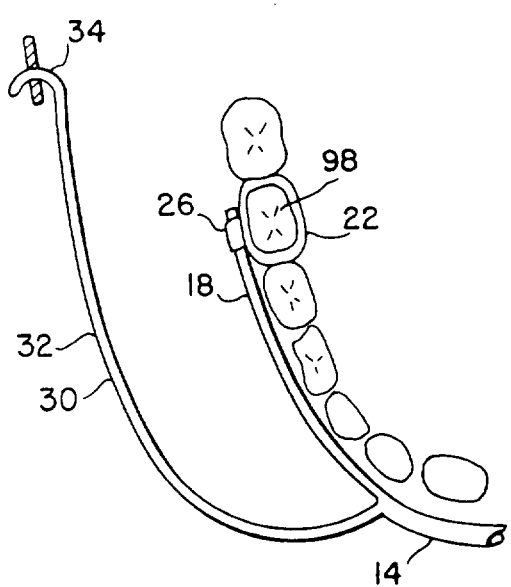
FIG. 2A is an enlarged view of the inner bow/buccal tube interconnection of FIG. 2.

One embodiment of the present invention is illustrated in FIGS. 1–2A. The headgear assembly 10 generally includes a facebow 14 comprising inner and outer bow 18, 30, respectively, two magnetic release mechanisms 38, and an elastic neck strap 78. The inner bow 18 is substantially arcuate and is positioned within the mouth of the patient 90 to transfer and apply treatment forces directly to the teeth 98, which are typically within the patient's upper arch and comprise the upper first molars. In this regard, the ends of the inner bow 18 are each typically slidably received within a buccal tube 26 which is fixedly attached to a band 22 positioned on/about one of the maxillary first molars 98. A stop of some type is also typically incorporated so that the inner bow 18 is able to exert the treatment forces on the upper first molars 98 without sliding distally, which would allow other teeth to be undesirably contacted by the inner bow 18.

The outer bow 30 is rigidly connected (e.g., welding, brazing) to the inner bow 18 at substantially the midline of the teeth of the patient 90 and its arms 32 extend outwardly and about the face of the patient 90. Alternatively, it may be possible to have the outer bow 30 and inner bow 18 be of unitary construction (i.e., having the outer bow 30 and inner bow 18 simultaneously formed from a single piece of stock). Nonetheless, the hooked ends 34 of the outer bow 30 are each appropriately interconnected with the neck strap 78 by the magnetic release mechanism 38 in tension therebetween. The neck strap 78 thus generates and applies the treatment forces to the ends 34 of the outer bow 30 through the magnetic release mechanisms 38. Consequently, the "strength" of the release mechanisms 38 must be sufficient to withstand these treatment forces, but insufficient to remain connected upon the release mechanism 38 experiencing a force of a predetermined magnitude (e.g., upon a third party grabbing the outer bow 30 and applying a non-orthodontic treatment force thereto). More particularly, the release force of each of the magnetic release mechanisms 38 must be greater than the associated treatment force, the amount in excess typically being determined by the orthodontic practitioner.

With further regard to the "strength" requirements of the magnetic release mechanism 38, namely the strength of the magnetic interconnection as will be discussed below, it can be appreciated by a review of FIGS. 1–2 that each of the mechanisms 38 are in tension during orthodontic treatment. Therefore, when the total tensile forces experienced by one of the mechanisms 38 meets or exceeds the predetermined amount, disconnection or release will occur in a manner also discussed below. For instance, in the event that a treatment force of a first magnitude is applied to each end 34 of the outer bow 30, the release point for each magnetic release mechanism 38 can be selected to coincide with a force of a second magnitude which is greater than the first magnitude. The actual variation between the first and second magnitudes may be selected by the practitioner based upon a variety of factors. When this predetermined force having at least the second magnitude is thus experienced by either of the magnetic release mechanisms 38, disconnection will occur to reduce the potential for the potentially severe adverse effects associated with snap-back of the outer and/or inner bows 30, 18.

One embodiment of the magnetic release mechanism 38 is more particularly illustrated in FIG. 3 and generally includes first and second casings 42, 58 which are magnetically connected when the inner faces of such are normally and abuttingly engaged. In this regard, first and second magnetically reactive materials 54, 70 are positioned and rigidly contained within first and second cavities 50, 66, respectively, within the adjacent ends of the first and second casings 42, 58, respectively. Holes 46, 62 are provided on the first and second casings 42, 58, respectively, to engage an end 34 of the outer bow 30 and a connecting member 74, respectively, The connecting member 74 interconnects the associated release mechanism 38 and the neck strap 78. More particularly and as illustrated in FIG. 4, one end of the connecting member 74 engages the hole 62 within the second casing 58 while its opposite end is positioned within one of three holes 86 of an adaptor 82 which is appropriately secured to the neck strap 78. Therefore, the magnetic release mechanisms 38 are incorporated in such a manner so as to be separable to provide for the desired disconnection of the headgear assembly 10 upon experiencing a force of a predetermined magnitude as noted above.

The individual encasement of the first and second reactive materials 54, 70 by the first and second casings 42, 58, respectively, serves to both limit patient manipulation of the release mechanism 38, which reduces the potential for injury to the patient 9 and/or damage to the headgear assembly 10, and breaking, chipping, corrosion and other similar physical degradation (e.g., contamination from cosmetics, food, drink) of the reactive materials 54, 70, which maintains the effective life of the release mechanism 38. As can be appreciated, the casings 42, 58 may also be used to shield, direct, and/or focus/concentrate the magnetic field. In order to further improve upon these desirable features, preferably the second casing 58 will seat within a casing extension 52 adjacent to the first cavity 50 in the first casing 42 so that the first and second reactive materials 54, 70 will be effectively sealed within the release mechanism 38, but without introducing separation friction beyond that created by reactive materials 54, 70, when in use with the headgear assembly 10.

The first and second reactive materials 54, 70 connect the release mechanism 38 by establishing a magnetic field of sufficient attractive strength to withstand the forces applied during the above-described types of orthodontic treatment, namely by having a release force which is greater than such orthodontic treatment forces by a predetermined margin. Consequently, the reactive materials 54, 70 will remain connected when experiencing the prescribed orthodontic treatment forces, but will disconnect when experiencing the greater release force (e.g., when the tensile forces experienced by a given release mechanism 38 exceeds a certain level). In order to enhance the strength of the magnetic field, preferably the first and second casings 42, 58 will focus and direct the magnetic field. Since magnetic principles are utilized, at least one of the first and second reactive materials 54, 70 is magnetized, while the other may be magnetized or ferromagnetic. Furthermore, the magnetized material, whether it be the first and/or second reactive material 54, 70, may be bipolar or multipolar. Moreover, the magnets may be formed from rare earth metals. In the later case, due to concentrated force generating capability, this allows for a desirable reduction in size and weight and allows for the strength of the interconnection to be more easily and precisely varied by varying the size of magnets. More particularly, the size of these magnets is directly related to their strength. Therefore, the magnets may be readily "calibrated" for use in a given orthodontic treatment plan, namely by utilizing a size of magnet for each magnetic release mechanism 38 which has a desired margin between the orthodontic treatment force to be utilized and the force at which the mechanism 38 will release.

Figure 5A:
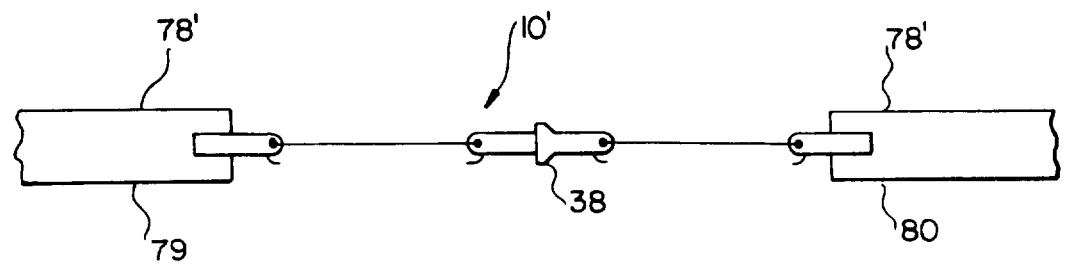
FIGS. 5A–C are views of various manners in which a magnetic release mechanism may be incorporated into a headgear assembly.

When the headgear assembly 10 is positioned upon the patient 90 in the above-described manner, it can be appreciated that the magnetic release mechanisms 38 will always be substantially axially aligned with the tensile or tension vector of the treatment forces being applied to the outer bow 30 by the neck strap 78, regardless of the position of the neck strap 78 on the back of the neck or head of the patient 90, or the relative position of the end(s) of the outer bow 30. Consequently, the magnetic release mechanisms 38 will always be subjected to substantially only tensile stresses such that the point at which the first and second reactive materials 54, 70 separate to disconnect the headgear assembly 10 upon the assembly 10 being subjected to a predetermined force will be substantially unaffected by the vector of the treatment force. However, it can be appreciated that this feature of the present invention may be provided by alternate configurations of the headgear assembly 10, all of which are within the scope of the present invention and some of which are illustrated in FIGS. 5A-C where components from the FIG. 2 embodiment are similarly numbered.

For instance, only one release mechanism 38, positioned between one end 34 of the outer bow 30 and the neck strap 78 in the above-described manner, may be required to provide the desired disconnection of the headgear assembly 10 (not shown). However, in practice when a release mechanism 38 is incorporated in this manner, one release mechanism 38 will typically be positioned on each side of the assembly 10 such that two release mechanisms 38 are utilized as illustrated in FIG. 2. Moreover, a release mechanism 38 may also be incorporated into the structure of the neck strap 78' to interconnect adjacent portions thereof as illustrated in FIG. 5A. More particularly, the neck strap 78' may be comprised of two sections 79, 80 interconnected by a single release mechanism 38 located at the back of the neck of the patient to provide for the desired release mechanism for the assembly 10'.

Figure 5B:
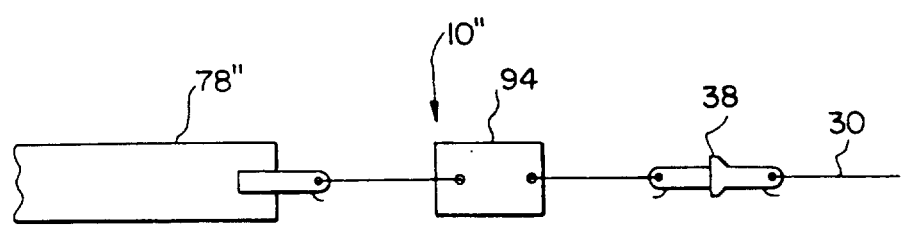
Figure 5C:
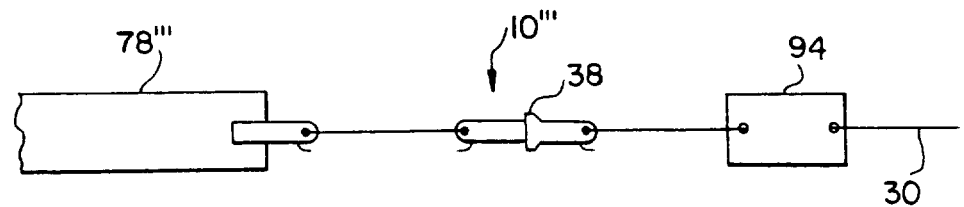

Under some circumstances, a force module 94 may be used instead of the elastic neck strap 78 to generate and apply the treatment forces to each end 34 of the outer bow 30 as illustrated in FIGS. 5B-C. For instance, these force modules 94 may be negator-type springs. In this case, one negator-type spring 94 and magnetic release mechanism 38 would be positioned on each side of the assembly 10" to interconnect one end of the substantially non-elastic neck strap 78" and one end of the outer bow 30. As can be appreciated, this interconnection may be provided by positioning the magnetic release mechanism 38 between the end 34 of the outer bow 30 and the force module 94 as illustrated in FIG. 5B, or by positioning the force module 94 between the end 34 of the outer bow 30 and the magnetic release mechanism 38 as illustrated in FIG. 5C. In either case, the magnetic release mechanism 38 remains subjected to substantially pure tensile forces.

Figure 6A:
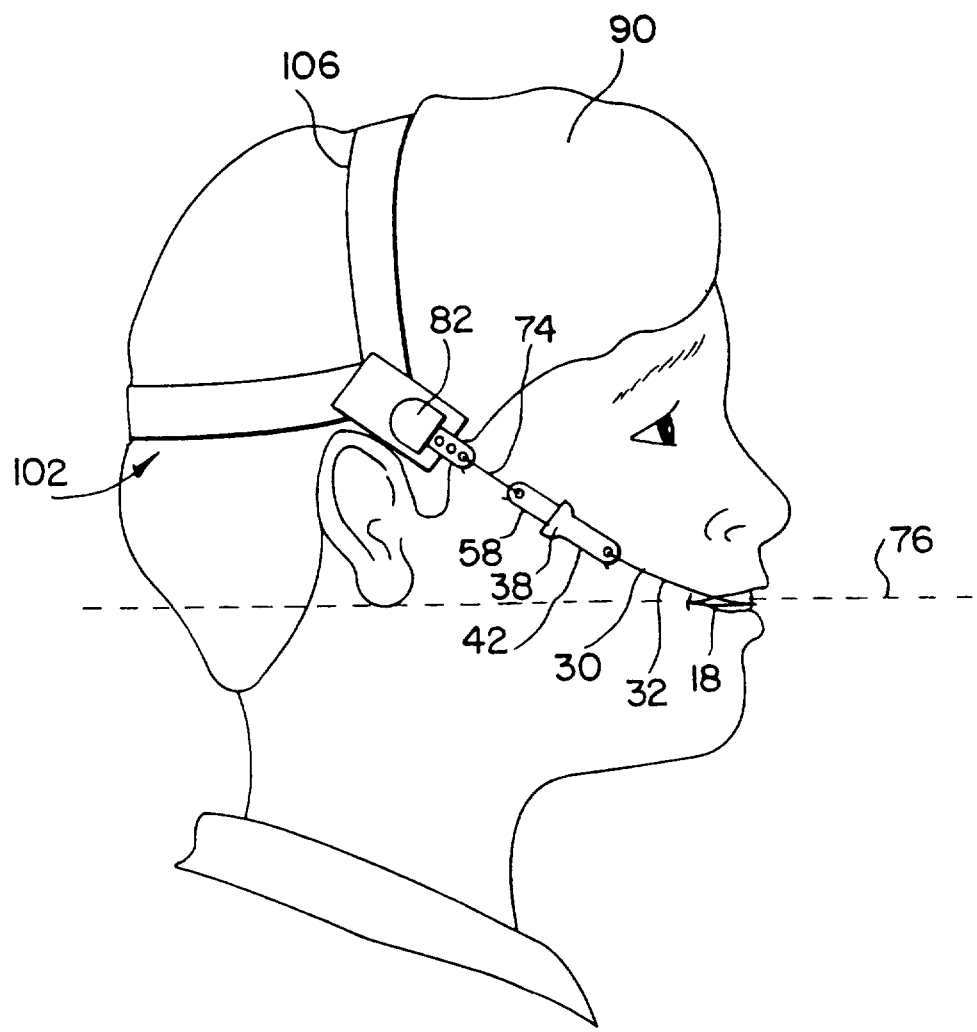
FIG. 6A is a side view of a patient wearing one embodiment of the headgear assembly of the present invention for providing a "high pull" treatment force.

Another embodiment of the present invention is illustrated in FIG. 6A where components from the FIG. 1 embodiment are similarly identified therein. Generally, the headgear assembly 102 of FIG. 6A includes a facebow 14 comprising inner and outer bows 18, 30, two magnetic release mechanisms 38 (only one shown) and a head cap 106. Consequently, the primary distinction between the headgear assembly 102 and the headgear assembly 10 is the replacement of the neck strap 78 with the head cap 106. However, as is known in the art this distinction provides significant differences in the types of orthodontic treatment forces that can be delivered and therefore the treatment techniques which may be utilized. More particularly, with the headgear assembly 102 of FIG. 6A, the vector of the treatment force has both a distal and a potentially significant vertical component (e.g., "high pull") relative to a plane 76 coplanar with the occlusal plane of the patient 90. Notwithstanding this change in the vector of the treatment force being applied to the teeth of the patient 90, the magnetic release mechanisms 38 continue to be substantially axially aligned within the tension-defined vector, and thereby subjected to substantially only tensile forces as noted above. Moreover, the predetermined force at which each such magnetic release mechanism 38 disconnects remains substantially constant independent of the actual treatment vector utilized.

Figure 6B:
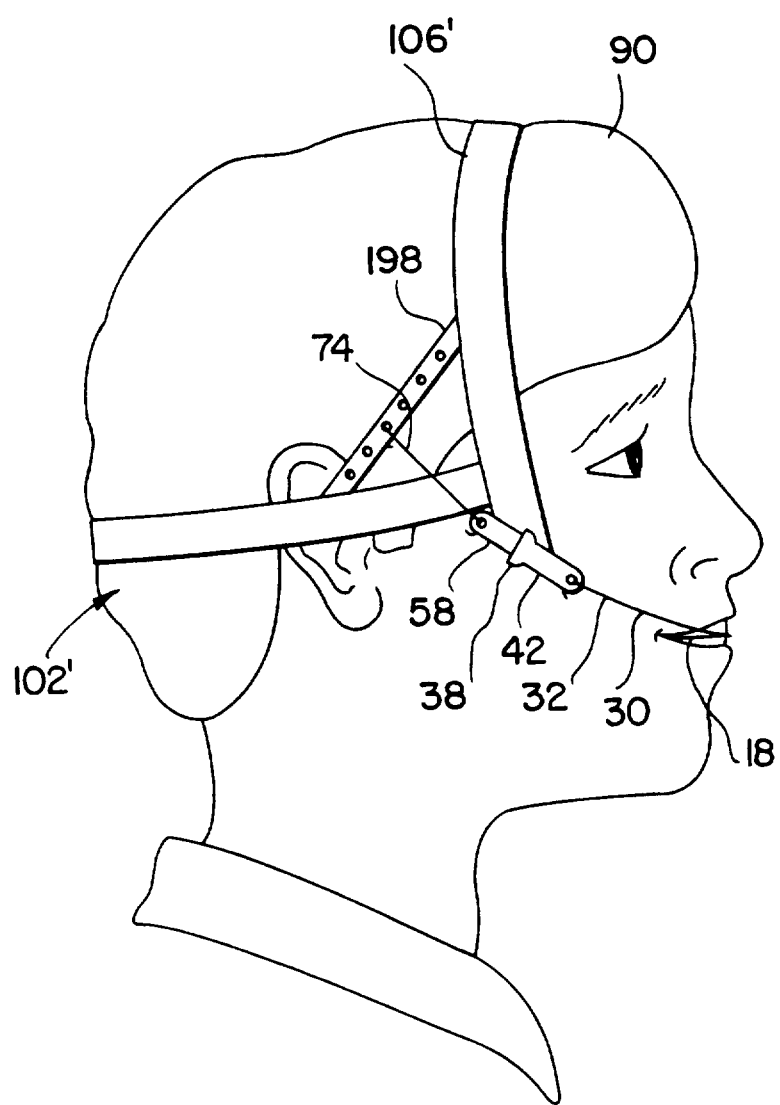
FIG. 6B is a side view of a patient wearing another embodiment of the headgear assembly of the present invention for providing a "high pull" treatment force.

A variation of the headgear assembly 102 is illustrated in FIG. 6B. The headgear assembly 102' of FIG. 6B provides for a "high pull" similar to that of the assembly 102. However, the head cap 106' is modified in that it includes an anchor strap 198 which interconnects the neck and upper head strap portions. The anchor strap 198 has a plurality of holes such that the anchor location (i.e., where the connecting member 74 attaches to the anchor strap 198) can be readily modified to vary the treatment vector.

Figure 7:
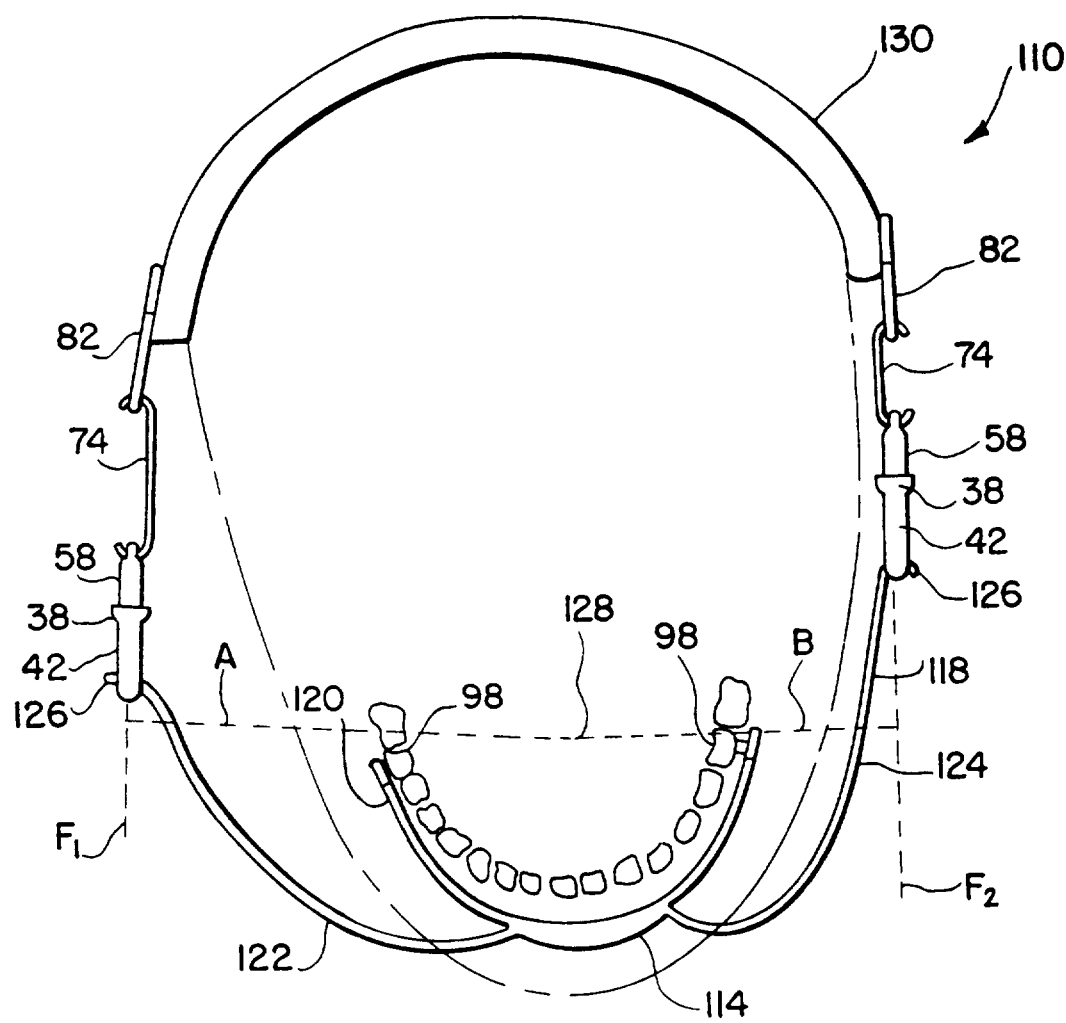
FIG. 7 is a view of one embodiment of the headgear assembly of the present invention installed on a patient's upper arch for applying different treatment forces to the teeth engaged by the inner bow and teeth interconnected therewith, namely by having the substantially equal length outer bow arms "bowed" in differing degrees.

Another embodiment of the present invention is illustrated in FIG. 7 where components from the FIG. 1 embodiment are similarly identified therein. Generally, the headgear assembly 110 of FIG. 6 includes a facebow 114 comprising inner and outer bows 120, 118, two magnetic release mechanisms 38 and a strap assembly 130. The outer bow 118 is rigidly connected to the inner bow 120 and has arms 122, 124 extending away from the point/region of interconnection. Although the arms 122, 124 are of substantially the same length, the arm 122 is bowed out to a greater degree from the center of rotation 128 than the arm 124 (e.g., the perpendicular distance A from the line of force $F_1$ to the center of rotation 128 is greater than the perpendicular distance B from the line of force $F_2$ to the center of rotation 128). This allows for the application of different forces to the displaced teeth 98.

As can be appreciated, it may be desirable in a given orthodontic treatment plan to utilize the facebow 114 of the FIG. 7 embodiment in combination with the neck strap 78 (FIG. 1 and to achieve a substantially purely distal pull) or the head caps 106, 106' (FIGS. 6A-B and to achieve a combined distal/vertical or lateral pull). Therefore, the strap assembly 130 may be either the neck strap 78, the head cap 106, the head cap 106', or various other configurations of anchor mechanisms when utilizing this facebow 114. Notwithstanding any variation in the forces applied to the teeth 98 of the patient by the arms 122, 124 of the outer bow 118 and inner bow 120, the magnetic release mechanisms 38 continue to be substantially axially aligned with the vector of the associated treatment forces, and thereby subjected to substantially only tensile forces as noted above. Moreover, the predetermined force at which each such magnetic release mechanism 38 disconnects remains substantially constant independent of such variation in forces.

Figure 8:
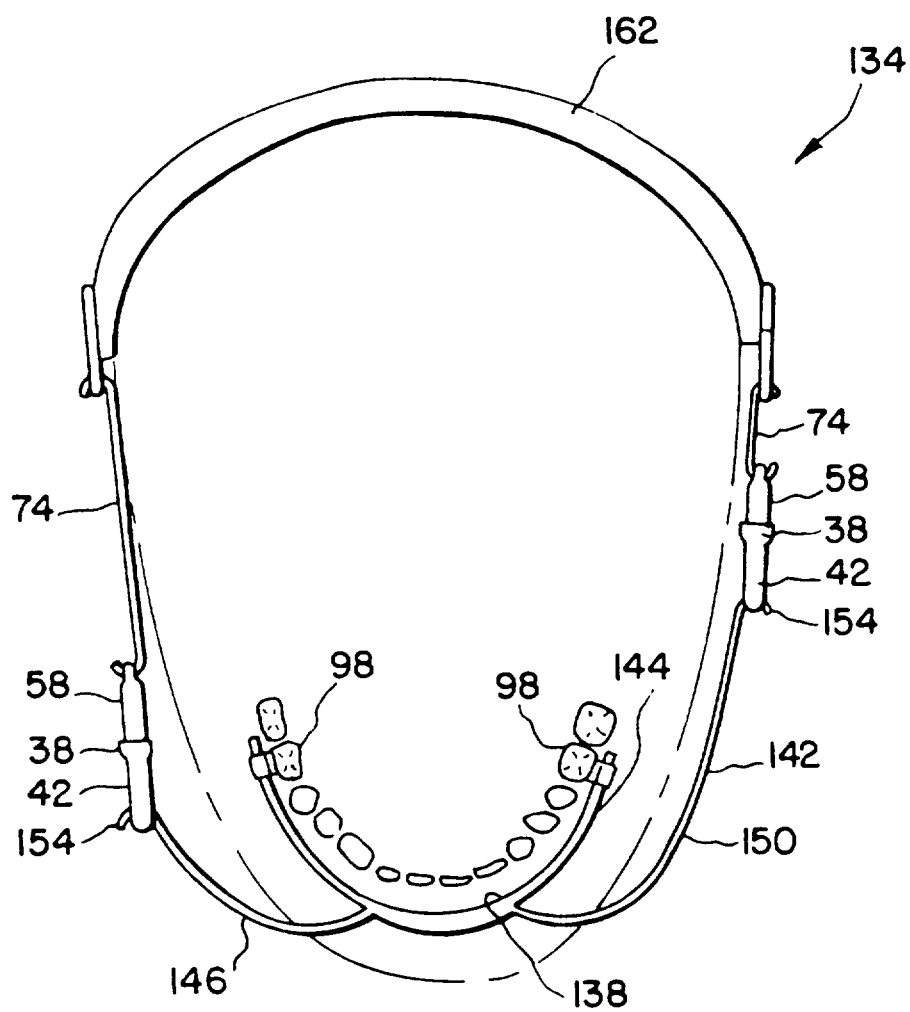
FIG. 8 is a view of one embodiment of the headgear assembly of the present invention installed on a patient's upper arch for applying different treatment forces to the teeth engaged by the inner bow and teeth interconnected therewith, namely by having the different length outer bow arms bowed in differing degrees.

Another embodiment of the present invention is illustrated in FIG. 8 where components from the FIG. 1 embodiment are similarly identified therein. Generally, the headgear assembly 134 of FIG. 8 includes a facebow 138 comprising inner and outer bows 144, 142, two magnetic release mechanisms 38 and a strap assembly 162. The outer bow 142 is rigidly connected to the inner bow 144 and has arms 146, 150 extending away from the point/region of interconnection to the hooked ends 154. In this regard, the arm 146 is shorter than the arm 150 and is also bowed outwardly to a greater degree than the arm 150. This allows for the application of lateral, in combination with intrusion and distalizing forces to the teeth 98.

As can be appreciated, it may be desirable in a given orthodontic treatment plan to utilize the facebow 138 of the FIG. 8 embodiment in combination with the neck strap 78 (FIG. 1 and to achieve a substantially purely distal pull) or the head caps 106, 106' (FIGS. 6A-B and to achieve a combined lateral/distal/vertical pull). Therefore, the strap assembly 162 may be either the neck strap 78, the head cap 106, the head cap 106', or various other configurations of anchor mechanisms when utilizing this facebow 138. Notwithstanding any variation in the forces applied to the teeth 98 of the patient by the arms 146, 150 of the outer bow 142 via the inner bow 144, the magnetic release mechanisms 38 continue to be substantially axially aligned with the vector of the treatment force, and thereby subjected to substantially only tensile forces as noted above. Moreover, the predetermined force at which each such magnetic release mechanism 38 disconnects remains substantially constant independent of such variation in forces or combinations of forces.

Figure 9:
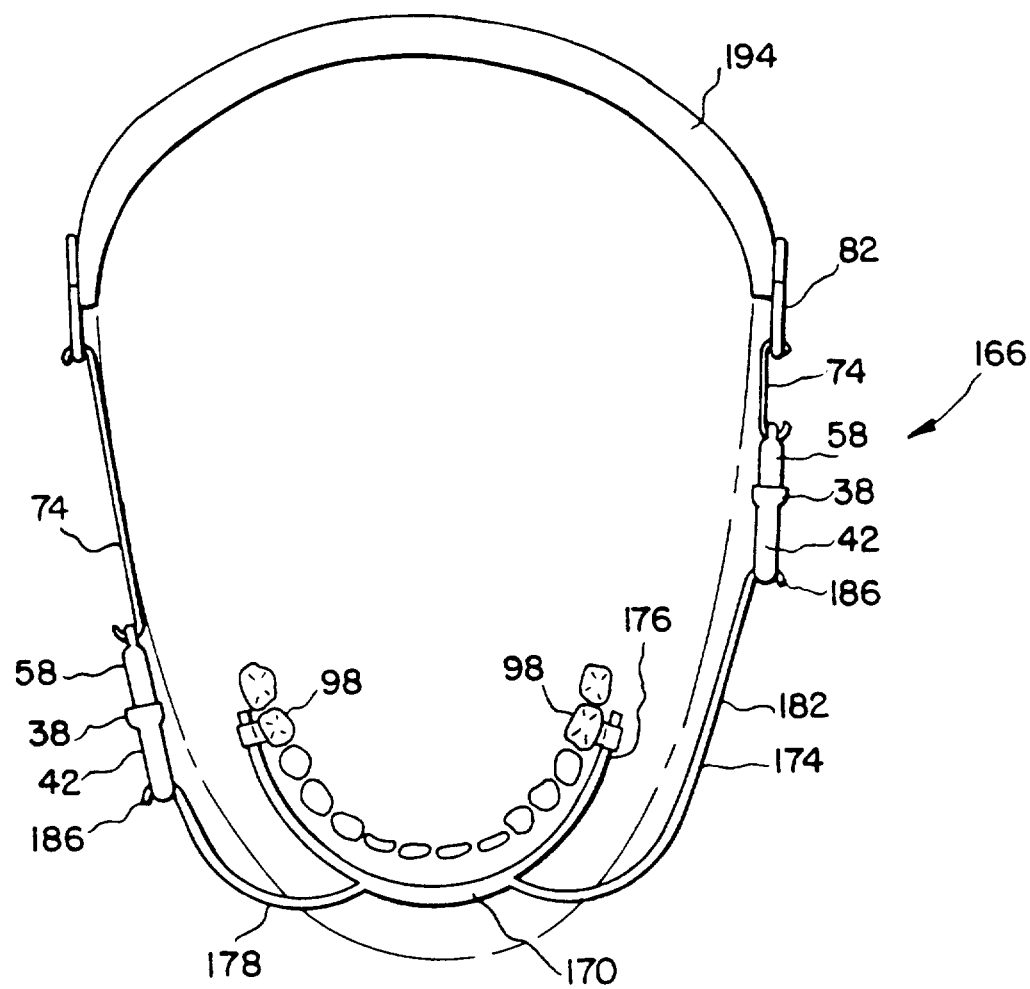
FIG. 9 is a view of one embodiment of the headgear assembly of the present invention installed on a patient's upper arch for applying different treatment forces to the teeth engaged by the inner bow and teeth interconnected therewith, namely by having the arms of the outer bow be of different lengths.

Another embodiment of the present invention is illustrated in FIG. 9 where components from the FIG. 1 embodiment are similarly identified therein. Generally, the headgear assembly 166 of FIG. 9 includes a facebow 170 comprising inner and outer bows 176, 174, two magnetic release mechanisms 38 and a strap assembly 194. The outer bow 174 is rigidly connected to the inner bow 176 and has arms 178, 182 extending away from the point/region of interconnection. In this regard, the arm 178 is shorter than the arm 182. This allows for the application of different forces to the teeth 98.

As can be appreciated, it may be desirable in a given orthodontic treatment plan to utilize the facebow 170 of the FIG. 9 embodiment in combination with the neck strap 78 (FIG. 1 and to achieve a substantially purely distal pull) or the head caps 106, 106' (FIGS. 6A-B and to achieve a combined distal/vertical pull). Therefore, the strap assembly 194 may be either the neck strap 78, the head cap 106, the head cap 106', or various other configurations of anchor mechanisms when utilizing this facebow 170. Notwithstanding any variation in the forces applied to the teeth 98 of the patient by the arms 178, 182 of the outer bow 174 via the inner bow 176, the magnetic release mechanisms 38 continue to be substantially axially aligned with the vector of the treatment force, and thereby subjected to substantially only tensile forces as noted above. Moreover, the predetermined force at which each such magnetic release mechanism 38 disconnects remains substantially constant independent of such variation in forces.

Based upon the foregoing, it can be appreciated that the magnetic release mechanisms 38 may be incorporated into a headgear assembly in which "different" treatment forces are being applied to the ends of the outer bow (e.g., due to the configuration of the outer bow, due to incorporating a force generator (negator-type spring) on each side of the assembly which are of different capacity/strength). In this case, it may be desirable/required to incorporate two magnetic release mechanisms 38 having different strengths. For instance, a magnetic release mechanism 38 having a 16 ounce release may be positioned on one side of the assembly, while a magnetic release mechanism 38 having a 20 ounce release force may be positioned on the other side of the assembly. More particularly, the "weaker" magnetic release mechanism 38 would be positioned on the side of the assembly on which the smaller treatment force was being utilized, while the stronger magnetic release mechanism 38 would be positioned on the side of the assembly on which the larger treatment force was being utilized. Notwithstanding the sizes/strengths of magnetic release mechanisms 38 being incorporated on a given headgear assembly, the margin between the treatment force and the release force should preferably be constant (e.g., each magnetic release mechanism 38 should have a release force which is a predetermined percentage greater than the associated treatment force).

The foregoing description of the present invention has been presented for purposes of illustration and description. However, the description is not intended to limit the invention to the form disclosed herein. Consequently, variations and modifications, commensurate with the above teachings, in the skill and/or knowledge of the relevant art, are within the scope of the present invention. The embodiments described hereinabove are further intended to explain best modes known of practicing the invention and to enable others skilled in the art to utilize the invention in such, or other, embodiments and with the various modifications required by their particular applications or uses of the invention. It is intended that the appended claims be construed to include alternative embodiments to the extent permitted by the prior art.

What is claimed is:

1. A headgear assembly for an orthodontic patient, comprising:
   an inner bow interconnectable with at least two displaced teeth within a mouth of the patient;
   an outer bow connected to said inner bow;
   force generating means for generating and applying a treatment force to said outer bow, wherein at least a portion of said treatment force is transferred to said inner bow and to at least one of the teeth; and
   magnetic release means for disconnecting at least a portion of said outer bow from said force generating means upon application of a predetermined force to at least a portion of said assembly.

2. An assembly, as claimed in claim 1, wherein:
   said outer bow is rigidly connected to said inner bow.

3. An assembly, as claimed in claim 1, wherein:
   a first portion of said treatment force is transferred to a first of the displaced teeth and a second portion of said treatment force is transferred to a second of the displaced teeth, wherein a magnitude of said predetermined force remains substantially constant and independent of any variation in magnitudes between said first and second portions of said treatment force.

4. An assembly, as claimed in claim 3, wherein:
   said magnitudes of said first and second portions of said treatment force are substantially unequal.

5. An assembly, as claimed in claim 3, wherein:
   said magnitudes of said first and second portions of said treatment force are substantially equal.

6. An assembly, as claimed in claim 1, wherein:
   said outer bow comprises first and second bow portions and an intermediate portion positioned therebetween and connected to said inner bow, said first and second bow portions being positionable on opposite sides of the patient's face and being of different lengths.

7. An assembly, as claimed in claim 1, wherein:
   a magnitude of said predetermined force remains substantially constant and independent of any direction utilized for said treatment force which has at least a distal component.

8. An assembly, as claimed in claim 7, wherein:
   a direction of said treatment force has both distal and vertical components relative to an occlusal plane of the patient.

9. An assembly, as claimed in claim 8, wherein:
   said treatment force is provided by an anchor point which is vertically displaced from said occlusal plane.

10. An assembly, as claimed in claim 1, wherein:
    said magnetic release means is subjected to substantially only tensile forces.

11. An assembly, as claimed in claim 1, wherein:
    said outer bow comprises first and second ends and said magnetic release means comprises first and second magnetic release mechanisms associated with said first and second ends, respectively.

12. An assembly, as claimed in claim 11, wherein:
    said first magnetic release mechanism has a first release force and said second magnetic release mechanism has a second release force which is greater than said first release force.

13. An assembly, as claimed in claim 1, wherein:
    said outer bow comprises first and second outer bow ends and said force generating means comprises a strap assembly having first and second strap portions each having first and second strap ends, at least part of said magnetic release means interconnecting said first strap ends of said first and second strap portions and said second strap ends of said first and second strap portions being interconnected with said first and second outer bow ends, respectively.

14. An assembly, as claimed in claim 1, wherein:
    said outer bow comprises first and second outer bow ends and said force generating means comprises a first force module and a strap assembly having first and second strap ends, at least part of said magnetic release means interconnecting said first force module and said first strap end, said first force module being interconnected with said first outer bow end, and said second strap end being interconnected with said second outer bow end.

15. An assembly, as claimed in claim 1, wherein:
    said outer bow comprises first and second outer bow ends and said force generating means comprises a first force module and a strap assembly having first and second strap ends, at least part of said magnetic release means interconnecting said first outer bow end and said first force module, said first force module being interconnected with said first strap end, and said second strap end being interconnected with said second outer bow end.

16. A headgear assembly for an orthodontic patient, comprising:

an inner bow interconnectable with at least two displaced teeth within a mouth of the patient;

an outer bow connected to said inner bow and comprising first and second ends, wherein an exterior portion of said assembly is defined between said first and second ends and engages at least one of a neck portion and a head portion of the patient;

force generating means, comprising at least part of said exterior portion, for generating and applying a treatment force to said outer bow, wherein at least a portion of said treatment force is transferred to said inner bow and at least one of the at least two displaced teeth; and magnetic release means for disconnecting a first part of said exterior portion of said assembly from a second part of said exterior portion of said assembly upon exposure of at least a portion of said assembly to a predetermined force.

17. An assembly, as claimed in claim 16, wherein:
a first portion of said treatment force is transferred to a first of the at least to displaced teeth and a second portion of said treatment force is transferred to a second of the at least two displaced teeth, wherein a magnitude of said predetermined force remains substantially constant and independent of any variation in magnitude between said first and second portions of said treatment force.

18. An assembly, as claimed in claim 17, wherein:
said magnitudes of said first and second portions of said treatment force are substantially unequal.

19. An assembly, as claimed in claim 17, wherein:
said magnitudes of said first and second portions of said treatment force are substantially equal.

20. An assembly, as claimed in claim 16, wherein:
said outer bow comprises first and second bow portions and an intermediate portion positioned therebetween and connected to said inner bow, said first and second bow portions being positionable on opposite sides of the patient's face and being of different lengths.

21. An assembly, as claimed in claim 16, wherein:
a magnitude of said predetermined force remains substantially constant and independent of any direction utilized for said treatment force which has at least a distal component.

22. An assembly, as claimed in claim 21, wherein:
a direction of said treatment force has both distal and vertical components relative to an occlusal plane of the patient.

23. An assembly, as claimed in claim 22, wherein:
said treatment force is provided by a means for engaging a portion of a head of the patient which is positioned vertically above said occlusal plane.

24. An assembly, as claimed in claim 16, herein:
said outer bow is rigidly connected to said inner bow.

25. A method for orthodontically treating a patient using a headgear assembly, comprising the steps of:
interconnecting an inner bow with at least two displaced teeth within a mouth of the patient;

interconnecting an outer bow having first and second ends to said inner bow;

engaging at least one of a back portion of a head of the patient and a neck portion of the patient with at least one strap portion;

interconnecting each of said first and second ends of said outer bow and said strap portion with a magnetic release device;

applying a first treatment force to a first of the at least two displaced teeth;

applying a second treatment force to a second of the at least two displaced teeth; and disconnecting said outer bow from said strap portion, utilizing at least one of said magnetic release devices, upon exposure of at least a portion of said assembly to a predetermined force, wherein a magnitude of said predetermined force is substantially constant and independent of a magnitude and direction of each of said first and second treatment forces.

26. A method as claimed in claim 25, wherein:
a direction of at least one of the treatment forces has both mesio-distal and occlusal-gingival components.

27. A method, as claimed in claim 25, wherein:
said magnitudes of said first and second treatment forces are substantially equal.

28. A method, as claimed in claim 25, wherein:
said magnitudes of said first and second treatment forces are substantially unequal.

29. A method, as claimed in claim 25, wherein:
said outer bow comprises first and second bow portions and an intermediate portion positioned therebetween and connected to said inner bow, said first and second bow portions being positionable on opposite sides of the patient's face and being of different lengths.

30. A headgear assembly for use in orthodontic treatment, comprising:
an inner bow interconnectable with at least two displaced teeth within a patient's mouth;

an outer bow interconnected to said inner bow and having first and second ends;

force generating means for generating and applying a treatment force to said outer bow, wherein at least a portion of said treatment force is transferred to said inner bow and thereby to at least one of the teeth and any teeth interconnected therewith; and first and second inner connected tensile segment members associated with said first and second ends of said outer bow, respectively, said first and second inner connected tensile segment members each comprising a magnetic release means having first and second portions for disconnecting when experiencing a force of a predetermined magnitude, each associated said first and second portions being calibrated to remain connected when subjected to said treatment force, each said associated first and second portions being calibrated to separate when subjected to a force in excess of said treatment force by a predetermined magnitude.

* * * * *

UNITED STATES PATENT AND TRADEMARK OFFICE
CERTIFICATE OF CORRECTION

PATENT NO. : 5,277,581
DATED : January 11, 1994
INVENTOR(S) : Peterson

It is certified that error appears in the above-identified patent and that said Letters Patent is hereby corrected as shown below:

Column 7, line 25, please delete "9" and insert therefor --90--.

Column 10, line 2, after "components from the FIG." please insert --1--.

Column 13,
Claim 17, line 22, please delete "to" and insert therefor --two--.

Signed and Sealed this

Sixteenth Day of August, 1994

Attest:

BRUCE LEHMAN

Attesting Officer

Commissioner of Patents and Trademarks